United States Patent
Kim et al.

(10) Patent No.: US 11,067,574 B2
(45) Date of Patent: Jul. 20, 2021

(54) MEMBRANE STRIP SENSOR USING EXPANSION MEMBER

(71) Applicant: GMD BIOTECH, INC., Gwangju (KR)

(72) Inventors: Min Gon Kim, Gwangju (KR); Ka Hee Kim, Gwangju (KR); Gyeo Re Han, Gwangju (KR); Hyou Arm Joung, Gwangju (KR)

(73) Assignee: GMD BIOTECH, INC., Gwangju (KR)

( * ) Notice: Subject to any disclaimer, the term of this patent is extended or adjusted under 35 U.S.C. 154(b) by 112 days.

(21) Appl. No.: 16/067,551

(22) PCT Filed: Oct. 20, 2016

(86) PCT No.: PCT/KR2016/011827
§ 371 (c)(1),
(2) Date: Jun. 29, 2018

(87) PCT Pub. No.: WO2017/115989
PCT Pub. Date: Jul. 6, 2017

(65) Prior Publication Data
US 2019/0137486 A1    May 9, 2019

(30) Foreign Application Priority Data

Dec. 29, 2015  (KR) .................. 10-2015-0188043

(51) Int. Cl.
| | |
|---|---|
| C12Q 1/68 | (2018.01) |
| G01N 33/558 | (2006.01) |
| G01N 33/58 | (2006.01) |
| C08L 1/08 | (2006.01) |
| C08L 29/04 | (2006.01) |
| C08L 61/28 | (2006.01) |

(52) U.S. Cl.
CPC .............. *G01N 33/558* (2013.01); *C08L 1/08* (2013.01); *C08L 29/04* (2013.01); *C08L 61/28* (2013.01); *G01N 33/58* (2013.01)

(58) Field of Classification Search
CPC .... G01N 33/526; G01N 33/558; G01N 33/58; G01N 33/54386; C08L 1/08; C08L 29/04; C08L 61/28
See application file for complete search history.

(56) References Cited

U.S. PATENT DOCUMENTS

| | | | | |
|---|---|---|---|---|
| 5,275,785 A | * | 1/1994 | May | G01N 33/54386 422/408 |
| 2009/0325143 A1 | * | 12/2009 | Saxena | G01N 33/558 435/2 |
| 2010/0233708 A1 | * | 9/2010 | Mehra | G01N 33/558 435/6.11 |

* cited by examiner

*Primary Examiner* — Betty J Forman
(74) *Attorney, Agent, or Firm* — Hauptman Ham, LLP

(57) ABSTRACT

A membrane strip sensor according to an embodiment of the present disclosure, the membrane strip sensor includes: a support; a sample pad; a conjugate pad; a reaction membrane; a absorption pad; and a secondary reagent pad.

10 Claims, 14 Drawing Sheets

BEFORE TEST

AFTER TEST

|  | 2min | 5min | 10min | 15min |
|---|---|---|---|---|
| USING DOUBLE-SIDED TAPE |  |  |  |  |
| USING WATER-SWELLABLE TAPE |  |  |  |  |

MEMBRANE STRIP SENSOR USING EXPANSION MEMBER

CROSS REFERENCE TO RELATED APPLICATION

This present application is a national stage filing under 35 U.S.C § 371 of PCT application number PCT/KR2016/011827 filed on Oct. 20, 2016 which 5 is based upon and claims the benefit of priority to Korean Patent Application Nos. 10-2015-0188043 filed on Dec. 29, 2015 in the Korean Intellectual Property Office. The disclosures of the above-listed applications are hereby incorporated by reference herein in their entirety.

BACKGROUND

1. Technical Field

The present disclosure relates to a membrane sensor with a swelling member, and, more specifically, to a membrane strip sensor having a water-soluble plastic tape as the swelling member, such that at least two reaction steps in a biological reaction are sequentially performed only via a single injection of a sample.

2. Description of the Related Art

Immunochromatographic assay may qualitatively and quantitatively inspect an analyte in a short period of time using a property that biological substances or chemical substances attach to each other in a specific manner. A device for the immunochromatographic assay may generally include an assay strip or an immunoassay kit in which the assay strip is assembled in a plastic housing.

FIG. 1 shows a representative implementation of a conventional immunochromatographic assay strip. As shown in FIG. 1, the assay strip used for the immunochromatographic assay includes a specimen pad 40, a conjugate pad 30, a signal detecting pad 20, and a absorption pad 50 on an adhesive plastic support 60. The specimen pad 40 absorbs a liquid specimen (or an analyte sample) and ensures a uniform flow of the liquid specimen. The conjugate pad 30 contains a fluidic conjugate that specifically binds to an analyte contained in the liquid specimen. When the liquid specimen introduced from the specimen pad 40 passes through the conjugate pad 30, a specific binding between the analyte and the fluid conjugate is achieved. The signal detecting pad 20 typically includes a detection zone 21 and a control zone 22. The detection zone 21 is a zone for verifying whether or not the analyte exists in the liquid specimen, and the control zone 22 is a zone for checking whether or not the liquid specimen has passed the detection zone 21 normally. On a portion of a top of the signal detecting pad 20, a absorption pad 50 is disposed. The absorption pad 50 absorbs the liquid specimen that has passed through the signal detecting pad 20 and helps capillary flow of the liquid specimen on the assay strip. In summary, the assay strip is manufactured by attaching the specimen pad 40, the conjugate pad 30, the signal detecting pad 20, and the absorption pad 50 to the adhesive plastic support 60 in this order. The assay strip performs the immunoassay by moving the liquid specimen from the specimen pad 40 through the signal detecting pad 20 to the absorption pad 50, and by detecting a signal at the signal detecting pad 20. In another modified example, the conjugate and the signal detecting substance are integrated into a single porous pad. In addition, the specimen pad, the conjugate pad, the signal detecting pad and the absorption pad are arranged to overlap each other or arranged at regular intervals on the plastic support. In the latter case, the liquid specimen is transferred to the specimen pad, the conjugate pad, and the signal detecting pad due to the capillary phenomenon using another medium.

Conventional immunochromatographic assay has a detection sensitivity of 1 ng/ml, and its detection sensitivity needs to be improved. Except for a sandwich method using a nanoparticle, it is difficult to implement a high-sensitivity reaction such as enzyme colorimetric reaction, fluorescence reaction, chemiluminescence reaction and the like as a single process possible with a single injection of a sample.

Further, in the analysis strip for a bioreaction requiring two or more reaction steps, such as the enzymatic reaction, chemiluminescent reaction, etc., a single sample injection into the analytical strip may not achieve the desired result. For example, in the case of a chemiluminescent strip, an antigen-antibody reaction is first performed, and, subsequently, a luminol reaction occurs. Thus, injection of a luminol reaction solution should be executed after the antigen-antibody reaction. In this connection, a following technique is disclosed in which, after the antigen-antibody reaction on a reaction membrane, a support coated with a luminol reaction substance contacts with a reaction location of the antigen-antibody reaction.

Therefore, it is required to develop a strip capable of measuring the biological reaction with two or more reaction steps in a single process by a single sample injection.

It should be understood that the foregoing description of the background art is merely intended to enhance the understanding of the background of the present disclosure and should not be construed as an admission that it is a prior art known to those of ordinary skill in the art.

SUMMARY

The present disclosure aims to solve these problems. A purpose of the present disclosure is to provide a membrane bio sensor capable of quantitative analysis and having high sensitivity by realizing a biological reaction or a chemical reaction having two or more reaction steps only via a single injection of to-be-detected sample, In order to achieve the above purpose, a membrane strip sensor according to an embodiment of the present disclosure includes: a support; a sample pad attached to a top face of the support to receive a liquid sample to be analyzed; a conjugate pad interlocking with the sample pad, and containing a primary reagent, wherein the primary reagent specifically binds to an analyte contained in the liquid sample through the sample pad; a reaction membrane which detects whether or not the analyte is present in the liquid sample and interlock with the conjugated pad; a absorption pad which is disposed downstream of the reaction membrane and absorbs the liquid sample for which a detection reaction is terminated; and a secondary reagent pad which connected to a swellable portion and is in contact with the reaction membrane by swelling of the swellable portion, wherein the secondary reagent pad is spaced apart from the reaction membrane, and the swellable portion swells by the liquid sample contained in the sample pad.

The swellable portion is joined to be supported by a support pad attached on an intermediate membrane disposed between the conjugate pad and the sample pad, and the swellable portion is attached to a connecting membrane is spaced apart from the reaction membrane by a predetermined distance.

The swellable portion may be made of a plastic material having pores defined therein to allow the swellable portion to be swollen by liquid which is adsorbed thereto.

The swellable portion may be made of a water-soluble plastic material.

The water-soluble plastic material may include at least one selected from a group consisting of polyvinyl alcohol (PVA), polyacrylamide (PAM), methylolated urea resin, methylolated melamine resin, and carboxymethyl cellulose (CMC).

The intermediate membrane may have a structure in which a large pore portion and a small pore portion are in a asymmetric structure, and the small pore portion is positioned toward the support pad.

The connecting membrane may have a structure in which a large pore portion and a small pore portion are in a asymmetric structure, and the small pore portion is positioned toward the swellable portion.

The primary reagent reacting with the sample may be treated to the conjugate pad, and a secondary reagent generating a signal is treated to the secondary reagent pad.

The primary reagent may be one or a conjugate of two or more selected from a group consisting of antibody, antigen, enzyme, peptide, protein, DNA, RNA, PNA, aptamer and nanoparticle.

The secondary reagent may be at least one selected from a group consisting of a light absorbing substance, a fluorescence substance, a luminous substance, an electrochemical signal generating substance, and a signal amplifying substance amplifying an intensity of an absorbance, fluorescence, luminescence or electrochemical signal.

According to the present disclosure, there are the following effects.

Firstly, enzyme reaction, antigen-antibody reaction, chemical reaction and the like with two or more reaction steps may be executed via a single injection of a to-be-detected sample, so that an application range of the conventional sensor with high detection sensitivity may be further expanded.

Secondly, it is possible to manufacture the strip sensor with a simple structure, thereby reducing a production cost while maintaining advantages of the conventional immunochromatographic assay device.

DETAILED DESCRIPTION

The terminology used herein is for the purpose of describing particular embodiments only and is not intended to be limiting of the present invention. As used herein, the singular forms "a," "an," and "the" are intended to include the plural forms as well, unless the context clearly indicates otherwise. It will be further understood that the terms "comprises," "comprising," "includes," and "including," when used in this specification, specify the presence of the stated features, integers, steps, operations, elements, and/or components, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, a membrane strip sensor according to a preferred embodiment of present disclosure will be described with reference to the accompanying drawings.

A key configuration of the present disclosure includes a secondary reagent pad and a swellable portion attached thereto, thereby delaying a reaction time of a secondary reagent in an immunochromatographic assay structure without decreasing performance or function thereof.

Figure 1:
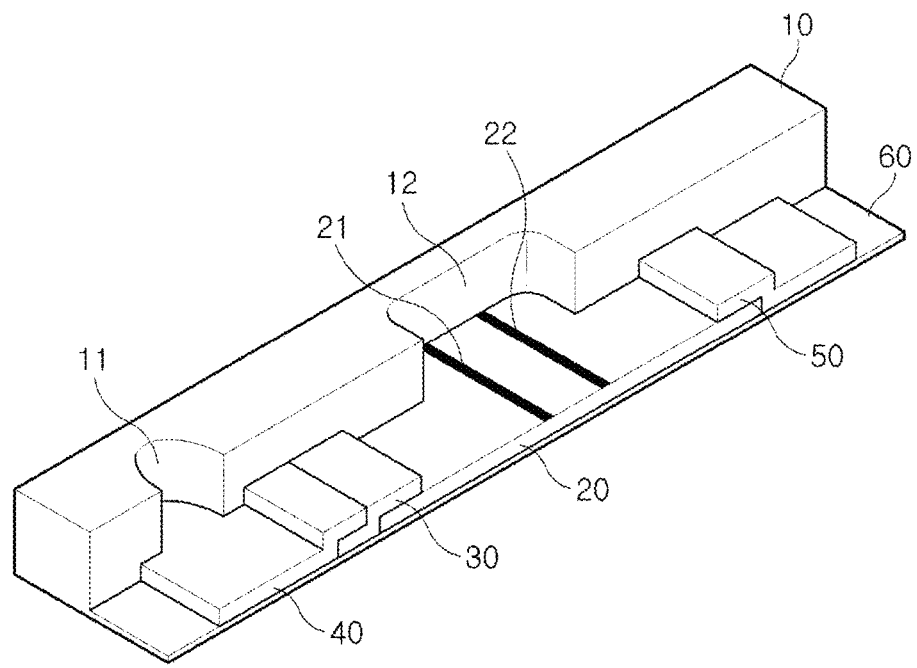
FIG. 1 shows a representative implementation of a conventional immunochromatographic assay strip.
Figure 2:
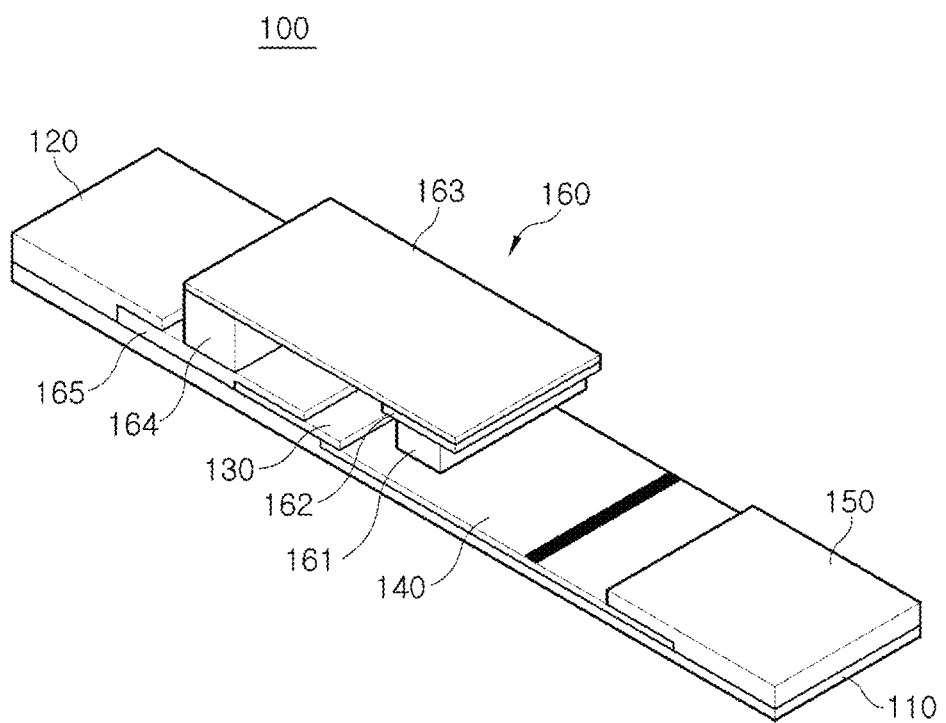
FIG. 2 is a basic block diagram of a membrane strip sensor according to an embodiment of the present disclosure.

FIG. 2 is a basic block diagram of a membrane strip sensor according to an embodiment of the present disclosure.

As shown in FIG. 2, the strip sensor includes a conventional general immunochromatographic assay structure and an additional structure to allow sequential reactions to occur. That is, the strip sensor includes a support 110, a sample pad 120, a conjugate pad 130, a reaction membrane 140, and a absorption pad 150 as the conventional immunochromatographic assay structure, and includes a secondary reagent pad 161, a swellable portion 162, and a connecting membrane 163, a support pad 164, and an intermediate membrane 165 as the additional structure 160 to allow sequential reactions to occur.

First, the sample pad 120, the intermediate membrane 165, the conjugate pad 130, the reaction membrane 140, and the absorption pad 150 are laterally sequentially placed on the support 110. This arrangement direction is the same as a proceeding direction of a liquid sample. The intermediate membrane 165 is connected, on a top face thereof, to the support pad 164, the support pad 164 is connected, on a top face thereof, to one end of the connecting membrane 163, the other end of the connecting membrane 163 is connected to the swellable portion 162, and the swellable portion 162 is connected to the secondary reagent pad 161.

The support 110 serves to support the membrane strip sensor according to the present disclosure, and an adhesive plastic may be used.

The sample pad 120 receives and forwards the liquid sample to the intermediate membrane 165 or the reaction membrane 140. Liquid samples such as whole blood, plasma, serum, tear, saliva, urine, rhinorrhea, body fluid and the like may be used. This sample pad 120 may additionally have a filtering function to further improve selectivity for an analyte or to minimize effects of an interfering substance that may be included in the liquid sample. For example, when the whole blood is used as a liquid sample, a denser pad may be used to filter a red blood cell, or an auxiliary substance may be added to help filter the red blood cell. When if it is necessary, an auxiliary pad containing a substance which may increase a reaction between the analyte and a primary reagent or reduce an influence of the interfering substance may be additionally provided to upstream of the sample pad. A type of the sample pad 120 is not limited particularly as long as the pad 120 is capable of absorbing the liquid sample. However, preferably, it is made of cellulose, polyester, polypropylene or glass fiber and the like.

A primary reagent, which may be selectively bound to the analyte may be applied onto the conjugated pad 130 which in turn, may be dried. As the primary reagent, one or more conjugates selected from a group consisting of an antibody, antigen, enzyme, peptide, protein, DNA, RNA, PNA (peptide nucleic acid), aptamer, and nanoparticles may be used.

When the primary reagent is a metal nanoparticle, the analyte may be detected by a color change of the metal nanoparticle due to a selective reaction of a receptor and the analyte. The analyte may be analyzed quantitatively by measuring an absorbance, electrical conductivity and the like of a complex between metal nanoparticles and the analyte selectively bound to the receptor on the membrane. Such the metal nanoparticle may be, for example, a gold nanoparticle, a silver nanoparticle, a copper nanoparticle, and the like but it is not limited thereto.

When the primary reagent is an enzyme, an enzyme substrate or an enzyme reaction-triggering substance, due to a selective reaction of the receptor and the analyte, the analyte or receptor react with the enzyme, enzyme substrate or enzyme reaction-triggering substance to cause enzyme reaction such as redox. At this time, the analyte may be detected by measuring an absorbance, fluorescence, luminescence, etc. of a product produced via the enzyme reaction. Such the enzyme may be glucose oxidase, glucose dehydrogenase, alkaline phosphatase, peroxidase and the like but is not limited thereto. In addition, the enzyme substrate may be, for example, glucose, hydrogen peroxide, and the like, but is not limited thereto.

Any type of the conjugate pad 130 may be available as long as the primary reagent is applied on the pad 130 which in turn is dried, and, subsequently, the reagent easily separates from the conjugate pad 130 when the conjugate pad 130 is wetted by the liquid sample. All conjugate pads commonly used in the immunochromatographic assay strips may be used. In this connection, the conjugate pad may be formed of a membrane made of, for example, nitrocellulose, nylon, polysulfone, polyethersulfone or PVDF (polyvinylidene fluoride) as well as cellulose, polyester, polypropylene or glass fiber.

The reaction membrane 140 may serve as a passage through which the biological sample is transferred, and at the same time, may realize lateral flow which allows checking the desired chemical and biological reaction results. It is preferable that the membrane 140 employs a membrane made of a material selected from a group consisting of nitrocellulose, nylon, polysulfone, polyethersulfone and polyvinylidene fluoride (PVDF). However, the present disclosure is not limited thereto. Further, any type of the membrane may be used for the reaction membrane 140 as long as it allows the lateral flow of the liquid sample The absorption pad 150 serves to absorb the liquid sample forwarded to the reaction membrane. A type of the absorption pad 150 is not limited particularly as long as it is capable of absorbing the liquid sample. However, it is preferably made of cellulose, polyester, polypropylene or glass fiber and the like.

The secondary reagent pad 161 stores a reagent required for a secondary reaction induced after a certain period has elapsed after a primary reaction has been performed with a first injected sample. The secondary reagent pad 161 stores a biological sample, a chemical sample, a reaction-condition control substance and the like. A type of this secondary reagent pad 161 is not limited particularly as long as the aqueous reagent is applied on the secondary reagent pad 161 which, in turn, is dried. A absorption pad or membrane generally used for the strip sensor may be used as such type of the secondary reagent pad 161. Preferably, the secondary reagent pad 161 may be made of cellulose, polyester, polypropylene, glass fiber, or the like.

The swellable portion 162 is adhered to the secondary reagent pad 161. The swellable portion 162 may be made of a plastic material in which pores are formed so as to be swellable by the aqueous solution absorbed through the absorption pad 150. As the plastic material used for the swellable portion 162, various water-soluble plastics may be used. As the water-soluble plastic, one or more selected from a group consisting of polyvinyl alcohol (PVA), polyacrylamide (PAM), methylolated urea resin, methylolated melamine resin and carboxymethyl cellulose (CMC) may be include. The swellable portion 162 may be in a form of a double-sided tape having an adhesive property. The secondary reagent pad 161 may contact the reaction membrane as the supplied liquid sample penetrates into the internal pores such that the swellable portion 162 expands in a vertical direction.

The support 110 is connected, on a top face thereof, to the intermediate membrane 165, so as to transfer the liquid sample to the swellable portion 162, and to space the secondary reagent pad 161 apart from the reaction membrane 140. Then, the support pad 164 is disposed on the intermediate membrane 165. The connecting membrane 163 is disposed on the support pad 164. Then, the connecting membrane 163 is connected to one side of the swellable portion 162.

The intermediate membrane 165 serves to transfer the liquid sample received from the sample pad 120 to the swellable portion 162. The intermediate membrane 165 has an asymmetric structure with a large pore portion and a small pore portion. The small pore portion is preferably located adjacent to the support pad 164. In addition, the connecting membrane 163 serves to transfer the liquid sample supplied from the intermediate membrane 165 and the support pad 164 to the swellable portion 162. The connecting membrane 163 has an asymmetric structure with a large pore portion and a small pore portion, and the small pore portion is preferably located adjacent to the swellable portion 162. In general, the use of the asymmetric membrane (ASPM) leads to a result that the aqueous liquid flows in one direction from the large pore portion to the small pore portion and does not flow in the opposite direction, which may be due to the capillary phenomenon. Therefore, a general fluid flows through a hydrophilic porous membrane, and the porosity structure of the porous membrane is asymmetric, so that the liquid sample may move only toward the small pore portion.

The secondary reagent generating a signal may be treated in the secondary reagent pad 161. The secondary reagent may include a light absorbing substance, a fluorescence substance, a luminous substance, an electrochemical signal generating substance, or a signal amplifying substance for amplifying intensity of the absorbance, fluorescence, luminescence or electrochemical signal. More specifically, an example of the secondary reagent may include a chemiluminescent substance such as luminol, lumigen, and luciferin, an electrochemiluminescent substance such as tuthenium tris-bipyridine (Ru(Bpy)3) and the like, an enzyme-coloring base such as 3,3',5,5'-tetramethylbenzidine (TMB), 3,3'-diaminobenzidine tetrahydrochloride (DBA), 2,2'-azinobis (3-ethylbenzthiazoline-6-sulphonic acid)(ABTA), 4-chloro-1-naphthol (CN), BCIP (5-bromo-4-chloro-3-indolyl-phosphate)/NBT (nitro blue tetrazolium) and the like, a fluorescence substance such as an organic fluorescence substance (e.g. FITC, rhodamine green, thiadicarbocyanine, Cy2, Cy3, Cy5, Alexa 488, Alexa 546, Alexa 594 and Alexa 647), a quantum dot and the like, a metal nanoparticle, a magnetic nanoparticle, a pH regulating substance (e.g., NaOH, HCl, buffer) and the like. The secondary reagent may further include the signal amplifying substance or a signal suppressing substance.

A biological substance (receptor) capable of capturing the analyte in the injected sample is treated on the reaction membrane 140.

As a result, when the primary reagent is applied to the conjugate pad 130 which, then, is dried, the reaction caused by the primary reagent and the secondary reagent occurs sequentially. Thus, the analyte in the liquid sample may be measured by the signal from the signal generating substance. In addition, the swellable portion serves to delay the release of the secondary reagent.

In the present disclosure, the liquid sample injected through the sample pad 120 may be any sample with or without the analyte, and it means a fluid that may flow from the sample pad 120 to the absorption pad 150. Specifically, it means a sample in liquid form including blood, serum or specific analyte (DNA, protein, chemical substance, toxic substance and the like).

Figure 3A:
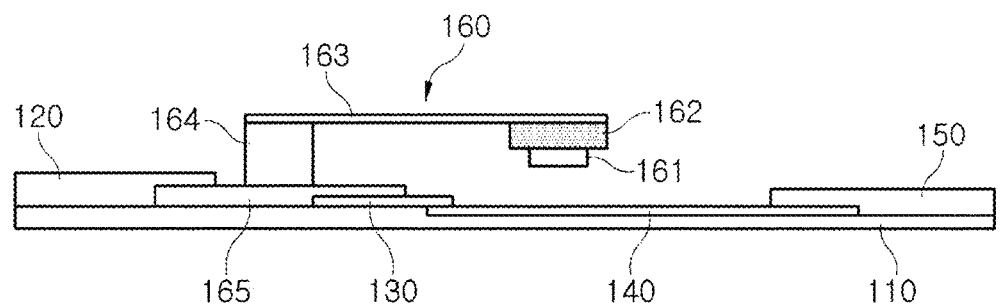
FIG. 3a is a cross-sectional view showing an operation of a membrane strip sensor according to an embodiment of the present disclosure, and shows the state before the liquid sample is initially injected.
Figure 3B:
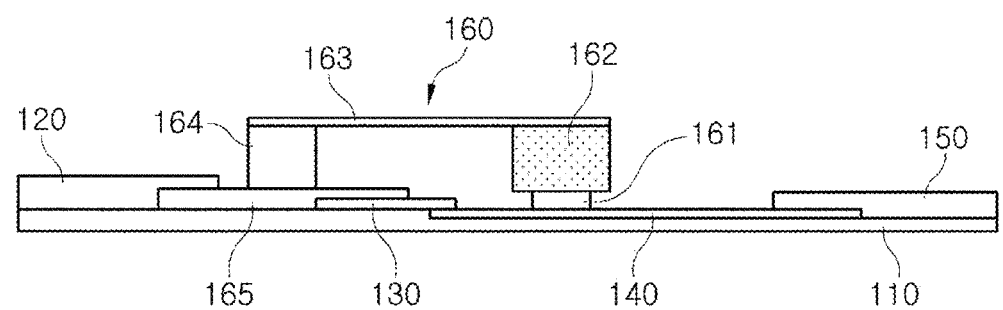
FIG. 3b is a cross-sectional view showing an operation of a membrane strip sensor according to an embodiment of the present disclosure, and shows the state that a certain time passed after the liquid sample is injected, and the swellable portion swelled thereby the secondary reagent pad is in contact with the reaction membrane.

FIG. 3 is a cross-sectional view showing an operation of a membrane strip sensor according to an embodiment of the present disclosure. FIG. 3(*a*) shows a state before the liquid sample is initially injected, while FIG. 3(*b*) shows a state in which the swellable portion swells after a lapse of a certain time after the liquid sample is injected, and the secondary reagent pad is in contact with the reaction membrane. The operation of the membrane strip sensor according to an embodiment of the present disclosure will be described in detail, for example, when a specific protein desired to be detected.

The liquid sample absorbed through the sample pad 120 travels through the intermediary membrane 165 and the supporting pad 164 to the connecting membrane 163, and through the conjugate pad 130 and the reaction membrane 140 to the absorption pad 150. At this time, the primary reagent in the conjugate pad 130 does not flow to the connecting membrane 163 due to structural separation.

When the liquid sample flows through the reaction membrane 140, for example, when the serum is injected into the sample pad 120, a target antigen binds to a detection antibody to form an antigen-antibody complex on the conjugate pad 130. The complex flowing through the reaction membrane 140 binds to a capture antibody at a test line.

When the liquid sample flows through the connecting membrane 163, finally, when the liquid sample reaches the swellable portion 162, the swellable portion 162 is gradually swollen by the liquid sample. Then, when a predetermined time is reached, the secondary reagent pad 161 contacts with the reaction membrane 140. At this time, the secondary reagent present in the secondary reagent pad 161 flows to the reaction membrane 140. At this time, the antigen-antibody complex reacts with the secondary reagent to generate a signal. The reaction condition of the sensor may be changed depending on a property of the substance used in the swellable portion 162. That is, it is possible to control a flow time of the secondary reagent depending on a swelling speed of the swellable portion 162. In addition to the secondary reagent, by adding acid, base and buffer composition, it is possible to control PH and change the reaction condition at the reaction membrane 140.

The present disclosure will be described in more detail through following examples.

Example 1: Selection of the Swellable Portion and Measurement of Swellability

Figure 4A:
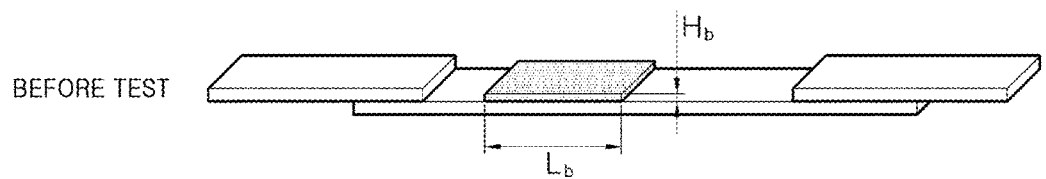
FIG. 4a is a schematic view showing an experiment for selecting a swellable portion according to an embodiment of the present disclosure, and is before the test.
Figure 4B:
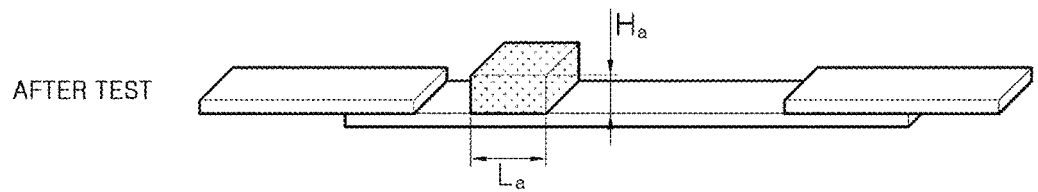
FIG. 4b is a schematic view showing an experiment for selecting a swellable portion according to an embodiment of the present disclosure, and is after the test.

In order to select a material which may be used for the swellable portion of the present disclosure, two types of water-swellable tapes were selected. Each tape was affixed onto a NC membrane used as the reaction membrane of a conventional immunochromatographic assay strip. PBS solution (100 μL) was dropped onto the sample pad. Then, changes in length and height of the tapes were measured for 20 minutes (see FIG. 4). FIG. 4a is a schematic view before the test, and FIG. 4b is a schematic view after the test.

Figure 5A:
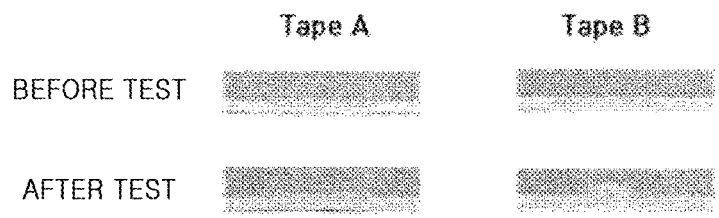
FIG. 5a shows results of the experiment for selecting a swellable portion according to an embodiment of the present disclosure, indicating that Tape B showed higher height increase than Tape A.
Figure 5B:
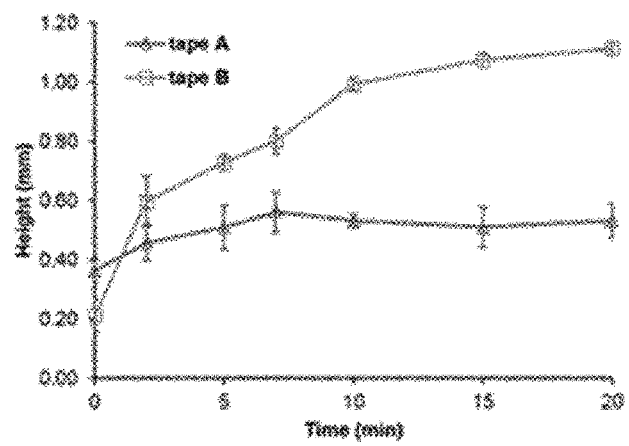
FIG. 5b show the change of the height of Tape A and Tape B with time.
Figure 5C:
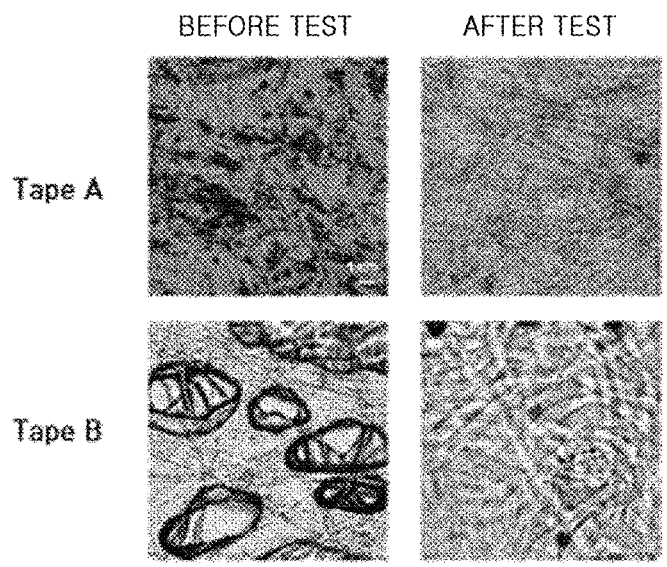
FIG. 5c shows the pores of Tape A and Tape B before and after the test, indicating that Tape B has more pores than Tape A.

FIG. 5 shows results of the swellability measurement for the swellable portion selection. As shown in FIG. 5a and FIG. 5b, Tape B showed larger height increase than Tape A. In particular, FIG. 5c shows that Tape B has a larger number of pores than Tape A. Further, Tape A shows substantially no change in structure after solution application while the pores of Tape B shrank and fiber structure was swollen. Therefore, difference in the swellability between the two tapes is measured as a result of the difference in the number of the pores between the two tapes.

Figure 6A:
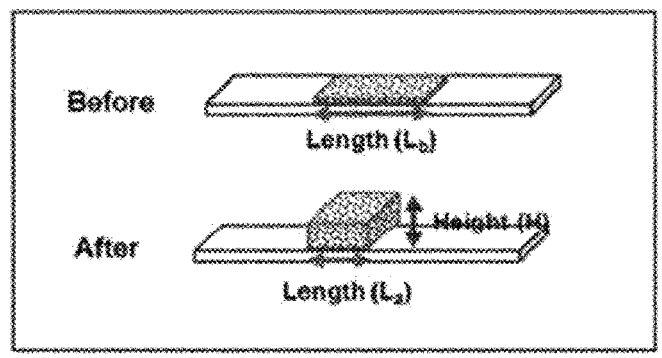
FIG. 6a shows a schematic diagram of a swelling experiment of a swellable portion according to an embodiment of the present disclosure.
Figure 6B:
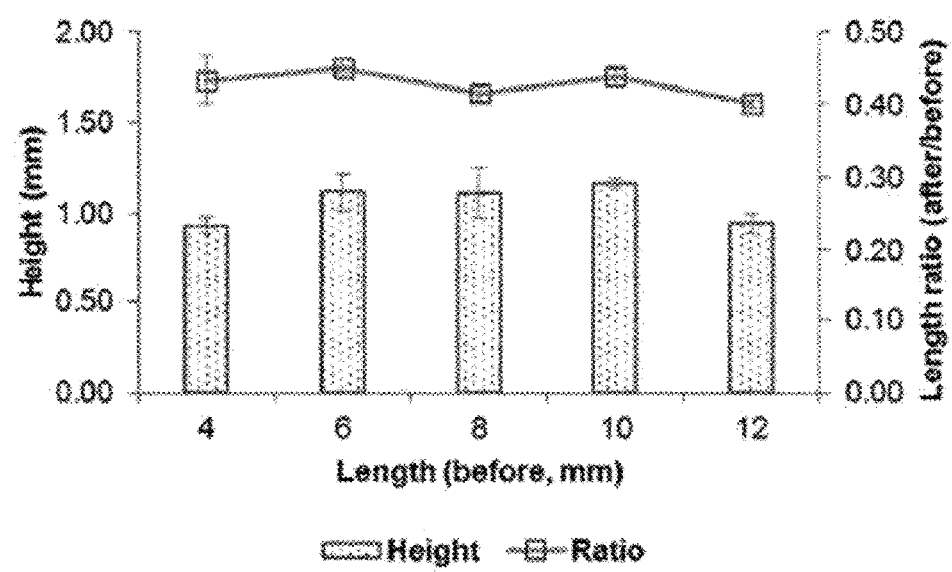
FIG. 6b show the result of the swelling experiment.

In addition, in order to measure a uniformity of the water-swellable tape used as the swellable portion, a ratio between an original length and a length thereof after water contact thereto was measured. In this connection, the original length of the tape used was 8 mm, and measurement results are shown in FIG. 6. As shown in FIG. 6, it was confirmed that the length ratio was 0.43±0.02 which indicates a small change in the length of the tape. The height of the tape after swelling was 1.06±0.11 mm.

Figure 7A:
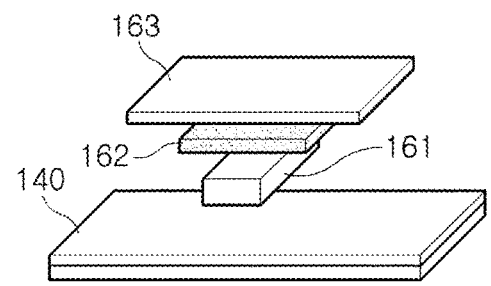
FIG. 7a is a simplified schematic view showing an experiment for confirming whether a secondary reagent has been delivered when introducing a swellable portion according to an embodiment of the present disclosure.
Figure 7B:
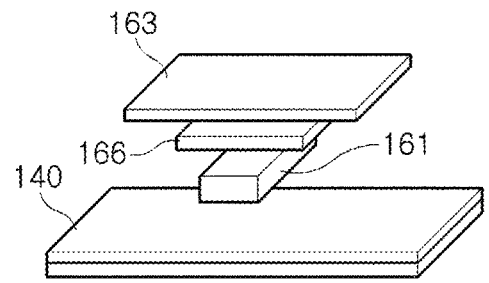
FIG. 7b is a simplified schematic view showing an experiment for confirming whether a secondary reagent has been delivered when not introducing a swellable portion according to an embodiment of the present disclosure.
Figure 8:
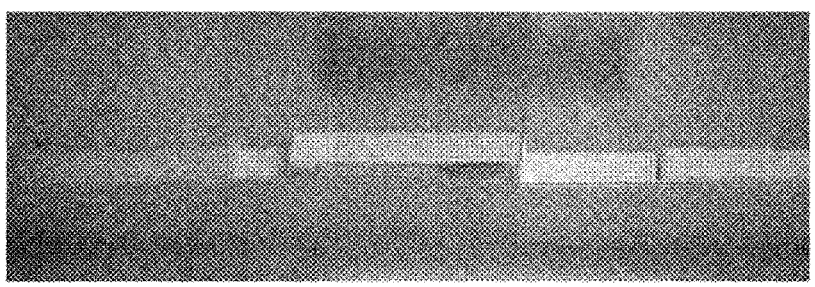
FIG. 8 shows experimental results to confirm whether a secondary reagent has been delivered when introducing a swellable portion according to an embodiment of the present disclosure and when not introducing the swellable portion.

In the immunochromatographic assay strip sensor according to the present disclosure, in order to confirm a role of the swellable portion, a blue dye was injected into the secondary reagent pad 161, and a release of the blue dye to the reaction membrane 140 was confirmed. In FIG. 7a, a swellable portion 162 made of the water-swellable tape was used. In FIG. 7b, an ordinary double-sided tape 166 was used. Experimental results are shown in FIG. 8. As shown in FIG. 8, in a structure using the water-swellable tape as the swellable portion, the blue dye contained in the secondary reagent pad was released 5 minutes after a PBS injection. However, when the ordinary double-sided tape was used, no blue dye was released. As a result, it was confirmed that an operation of the immunochromatographic assay strip sensor according to the present disclosure is determined by the property of the swellable portion. The water-swellable tape used as the swellable portion has a property of being laterally shrunk due to the porous structure, and as a result, it is vertically swollen. As a result of this property, the swelling of the water-swellable tape allows sequential reactions to occur automatically without additional injection of the reagent, thereby releasing the secondary reagent toward the secondary reagent pad.

Example 2: Manufacturing of the Membrane Strip Sensor Using the Swellable Portion The sample pad, absorption pad, and secondary reagent pad were prepared with absorbent type 133 and Fusion 5 was used as the conjugate pad. NC membrane was used as the reaction membrane, and absorbent paper type 165 was used as the support pad. Vivid plasma separation-GX membrane was used as the intermediate membrane and the connecting membrane.

The absorption pad (4 mm×20 mm) was attached to a top face of the reaction membrane (4 mm×25 mm), and the conjugate pad (4 mm×8 mm), intermediate membrane (4 mm×15 mm) and the sample pad (4 mm×25 mm) were attached to the adhesive plastic support in succession. In this connection, in the case of the intermediate membrane, a portion with small pores was positioned upwards. The connecting membrane (4 mm×20 mm) was attached to a slide glass using the double-sided tape, and the swellable portion was formed thereon using a PVA tape. In this connection, a portion with large pores contacts with the swellable portion. The secondary reagent pad is affixed on the swellable portion, and a sealing tape is attached to an area where the secondary reagent pad contacts with the swellable portion. Barriers were installed on both sides of the assembled strip to fix the slide glass. The strip was placed on the barrier and the support pad, and fixed with the double-sided tape.

The secondary reagents were tested as constituents for other signal generation reactions, each of the secondary reagents is a dye for a flow analysis, a gold ion for a metal ion amplification, NBT/BCIP for a enzyme colorimetric method and luminol for chemiluminescence method.

a dye for flow analysis, gold ions for the metal ion amplification reaction, NBT/BCIP for the enzyme colorimetric method, and luminol to be. For all of the secondary reagents, each secondary reagent solution is dropped onto the secondary reagent pad which, in turn, is dried at 65° C. for 30 minutes. The sealing tape is attached to the reagent pad, and the reagent pad is cut to have a size of 4.0 mm×3.8 mm. The injection of the secondary reagent will be described later in more detail in analysis examples.

Example 3: Performing the Metal Ion Amplification Reaction

In order to confirm the operation of the immunochromatographic assay strip sensor according to the present disclosure, the metal ion amplification reaction was performed. A solution of Gold (III) chloride trihydrate (0.1 M in 0.1 M phosphate buffer (pH 7.4)) was injected to the secondary reagent pad which in turn is dried. The injected solution contains hydroxylamine hydrochloride (10 mM) (in 0.1 M Tris-HCl (pH 8.0)) as a reducing agent. 15 nm gold nanoparticles with various concentrations were injected into the reaction membrane at 1 cmμL−1.

Figure 9:
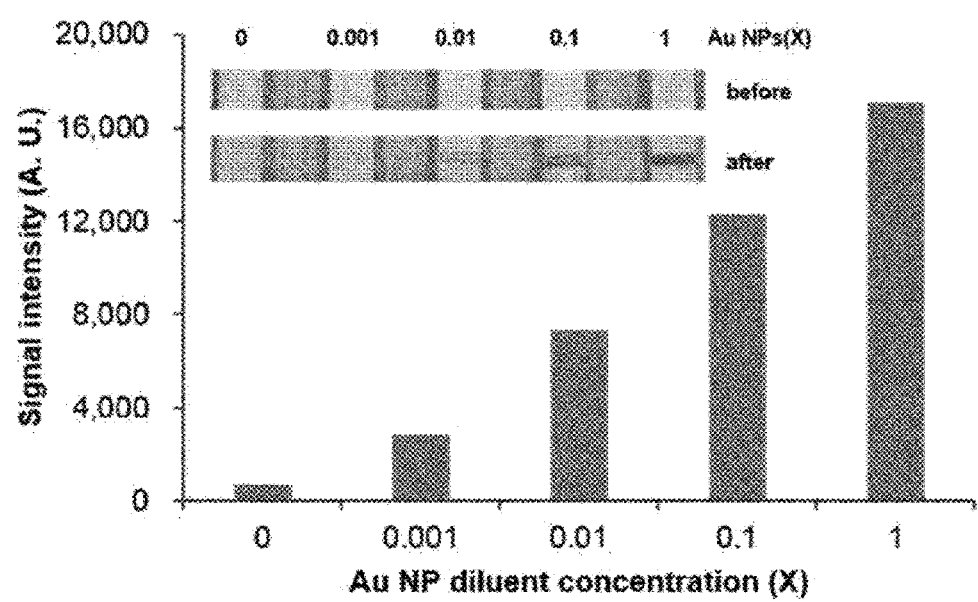
FIG. 9 is a graph showing results of a gold ion amplification reaction using a membrane strip sensor according to an embodiment of the present disclosure.

The gold ion amplification method may use a reaction in which $Au^{3+}$ is reduced on a gold ion surface by hydroxylamine ($NH_2OH$), such that a size of Au NP increases. Signal amplification methods in various immunochromatographic assay devices based on the gold ion amplification have been reported. To apply the gold ion amplification to the present disclosure, $NH_2OH$ solution was prepared, and $Au^{3+}$ was injected into the secondary reagent pad. The $NH_2OH$ solution flows through the reaction membrane, and at the same time, the swellable portion begins to expand. After few minutes, the secondary reagent pad containing the gold ion contacts the reaction membrane and then releases the gold ions. A reaction with Au NP in the reaction membrane amplifies an Au NP signal. Since a duration during which the gold ion and $NH_2OH$ contact may be delayed by the swellable portion, the amplified signal is generated without any other unintended signal. As shown in FIG. 9, an intensity of the amplified signal is shown to increase depending on an Au NP concentration.

Example 4: Performing an Enzyme-Coloring Reaction

In order to confirm the operation of the immunochromatographic assay strip sensor according to the present disclosure, an enzyme-coloring reaction was performed. A reaction of NBT and BCIP via alkaline phosphatase was selected as the coloring reaction. A solution containing 50 μL NBT and 20 μL BCIP is mixed with 930 μL of 0.5 M Tris-HCl buffer (pH 9.5) to form a mixture, which, in turn, is injected to the secondary reagent pad, which, in turn, is dried. Tris-HCl buffer (0.1 M, pH 8.5) was used as the injected solution. Streptavidin labeled AP (1 μL cm$^{-1}$) with various concentrations were injected into the reaction membrane.

Figure 10:
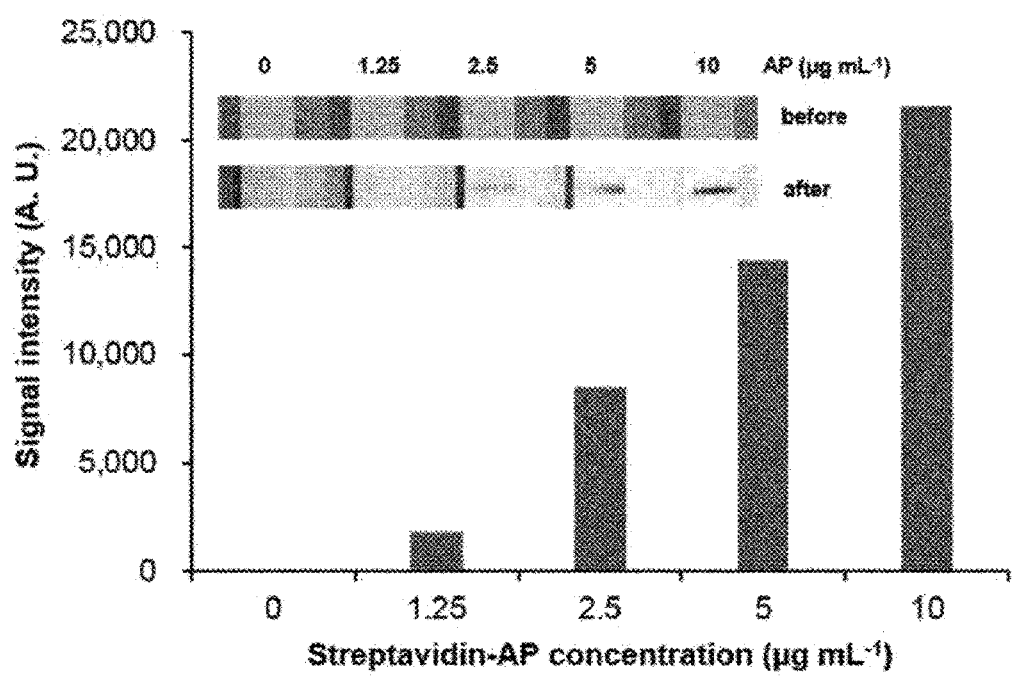
FIG. 10 is a graph showing results of performing an enzyme-coloring reaction using a membrane strip sensor according to an embodiment of present disclosure.

A reaction of NBT and BCIP catalyzed by the alkaline phosphatase is mainly used for immunoblotting, in situ hybridization, and immunohistochemistry. This reaction produces a final product called insoluble NBT diformazan, which causes color changes from blue to purple, making it possible for the naked eye to observe the reaction. The reaction between NBT and BCIP, catalyzed by enzymatic reactions, requires high pH. Thus, this condition is not suitable for the immunoassay. In accordance with the present disclosure, a high pH NBT/BCIP solution is injected into the secondary reagent pad which in turn, is dried. During the reaction, the sample solution flows through the reaction membrane, and the NBT/BCIP mixture is released by swelling of the swelling member. The pH of the reaction membrane changes when the secondary reagent pad contacts the reaction membrane, thereby allowing the NBT/BCIP reaction. As shown in FIG. 10, in a similar manner to the result of the gold ion amplification reaction, a signal intensity of the streptavidin-AP increases with increasing the AP concentration.

Example 5: Performing a Chemiluminescence Reaction

In order to confirm a uniformity of the operation of the immunochromatographic assay strip sensor according to present disclosure, a chemiluminescence reaction was performed. A reaction of choline and choline oxidase was used to generate hydrogen peroxide. A solution containing 10 μL anti-choline oxidase antibody (10 mg mL-1) and 2.5 μL choline oxidase (10 mg mL$^{-1}$) was mixed with 37.5 μL 0.1 M Tris-HCl (pH 8.5). Then, 1 μL of the solution was spotted between a capture antibody on the reaction membrane and the secondary reagent pad. 100 μL luminol (0.5 M in 50 mM NaOH), 30 μL choline chloride (1 M in DW), and 1 μL p-coumaric acid (0.5 M in dimethylformamide (DMF)) were mixed with 870 μL 0.1 M Tris-HCl buffer (pH 8.5). After mixing, 65 μL solution was injected to the sample pad which, in turn, is dried.

A mixture between HRP-labeled antibody (1 μg mL-1) and 1 μL of choline oxidase antibody was spotted on the reaction membrane. As the injected solution, 0.1 M Tris-HCl (pH 8.5) containing 0.5% (v/v) S10G and 1% (w/v) PVP 10K was used. The solution was loaded onto the sample pad, and the change in signal intensity was measured for 40 minutes. Signal intensity depending on a concentration of the HRP was measured using 1 μL of HRP labeled antibody for 20 minutes.

In order to measure the uniformity of the strip according to the present disclosure and timing of releasing the secondary reagent, signal changes over time were observed. The chemiluminescence method was selected as an experimental method in that signal analysis using the chemi-doc system is easy when using the chemiluminescence method.

Figure 11:
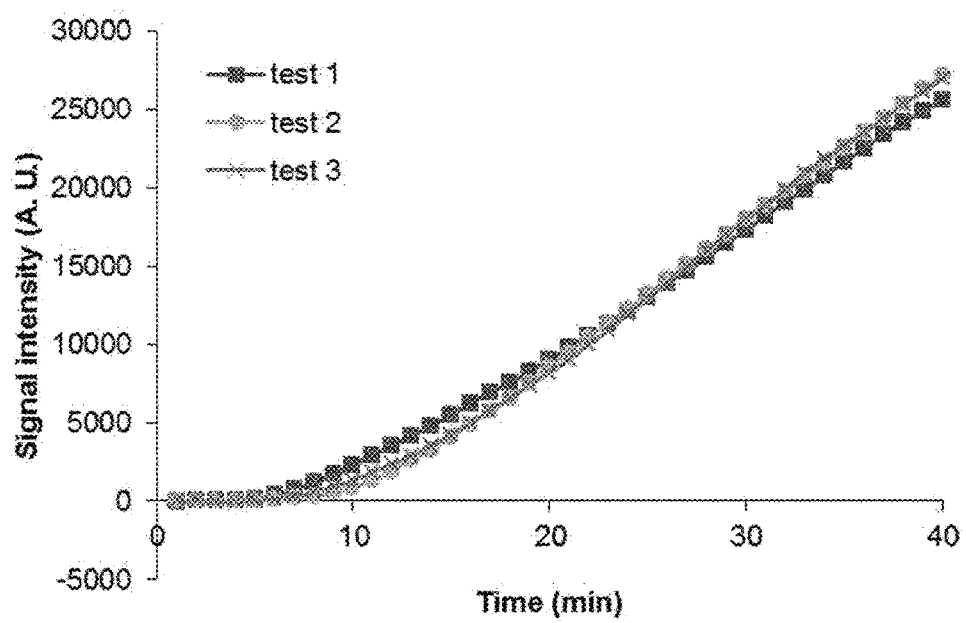
FIG. 11 is a graph showing the same HRP concentration as a result of performing chemiluminescence reaction using a membrane strip sensor according to an embodiment of present disclosure.

As shown in FIG. 11, changes in signal intensity over time were observed for 40 minutes using the same concentration of antibody-HRP. The signal intensities slightly are different at the beginning of the test, even with the same concentration of antibody-HRP. However, after 20 minutes, the signal intensities reached a value within 5% CV.

Figure 12:
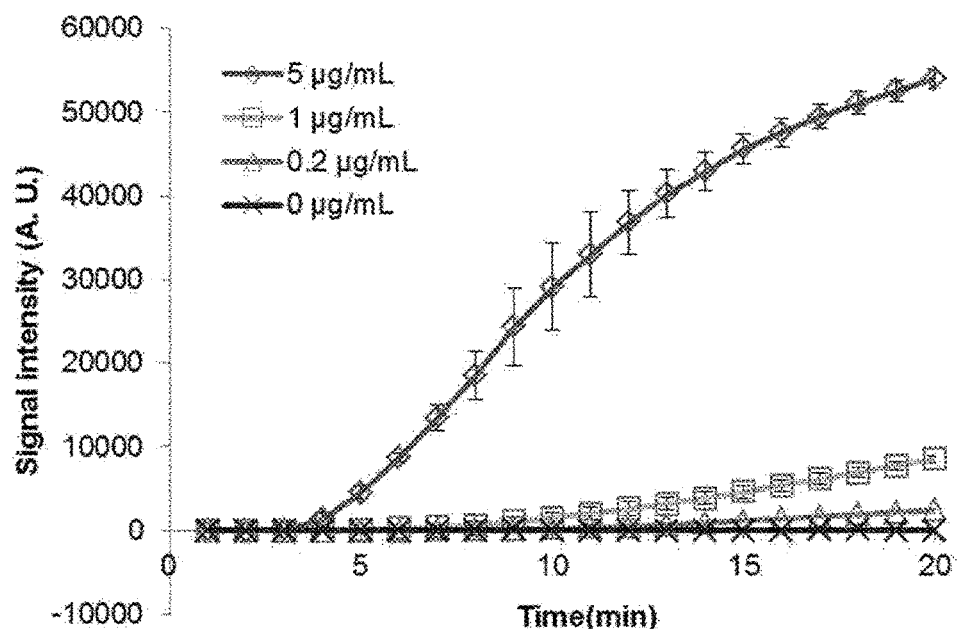
FIG. 12 is a graph showing various HPP concentrations as a result of performing chemiluminescence reactions using a membrane strip sensor according to an embodiment of present disclosure.

As shown in FIG. 12, also in experiment using different concentrations of the HRP, the signal intensities in accordance with the HRP concentration change at a uniform changing rate within 20 minutes. The result shows that the release time of and the release amount of the secondary reagent affect the signal strength.

Example 6: Measurement of CRP in Human Serum

In order to check the operation of the immunochromatographic assay strip sensor according to the present disclosure, CRP in human serum was detected.

CRP is a 120-kDa pentapeptide, known as the most important inflammatory marker, and is also used as an independent predictor of cardiovascular disease. In order to detect the CRP, serums injected with the CRP by concentration were used.

A mixture between CRP capture antibody (1 μL cm$^{-1}$) and choline oxidase is fixed onto a 120 sec cm$^{-1}$ reaction membrane, and 0.05% (v/v) S10G is injected on to the membrane, which, in turn, is dried at 37° C. for 15 minutes. The CRPs with various concentrations are injected into CRP-free human serum to prepare a CRP sample solution. 180 μL of the solution is injected into the membrane strip sensor according to the present disclosure, and the signal intensity is measured for 20 minutes.

In addition, a result from the new sensor was compared with result obtained using conventional ICA. In order to prepare Au NP conjugate, anti-CRP antibody (10 μL, 1 mg mL$^{-1}$) diluted with PBS is added to a mixture between 0.9 mL of 40 nm Au NP and 0.1 mL of borate buffer (0.1 M, pH 8.5) to form a product. After incubating the product at room temperature for 30 minutes, 0.1 mL of 100 mg mL$^{-1}$ BSA in PBS is added to the incubated product, to block a surface of the Au NP. After incubating the product at room temperature for 60 minutes, the incubated product is centrifuged at 8000 rpm at 10° C. for 20 minutes.

After discarding supernatant, the Au NP conjugate is re-suspended again with 10 mM borate buffer (pH 8.5) containing 1 mg mL$^{-1}$ BSA. The centrifugation and re-suspension steps are repeated twice with 10 mM borate buffer (pH 8.5). This Au NP conjugate is suspended by 100 μL using 10 mM borate buffer (pH 8.5). Then, the suspended Au NP conjugate is diluted two times using PBS containing 2% (w/v) PVP 10K and 1% (v/v) S10G, to obtain a diluted Au NP conjugate. Then, 5 μL of this diluted Au NP conjugate is injected into the conjugate pad, in which, in turn, is dried at 37° C. for 15 minutes. Then, 100 μL of the sample is injected into the sample pad and signal intensity is measured 15 minutes later.

Figure 13:
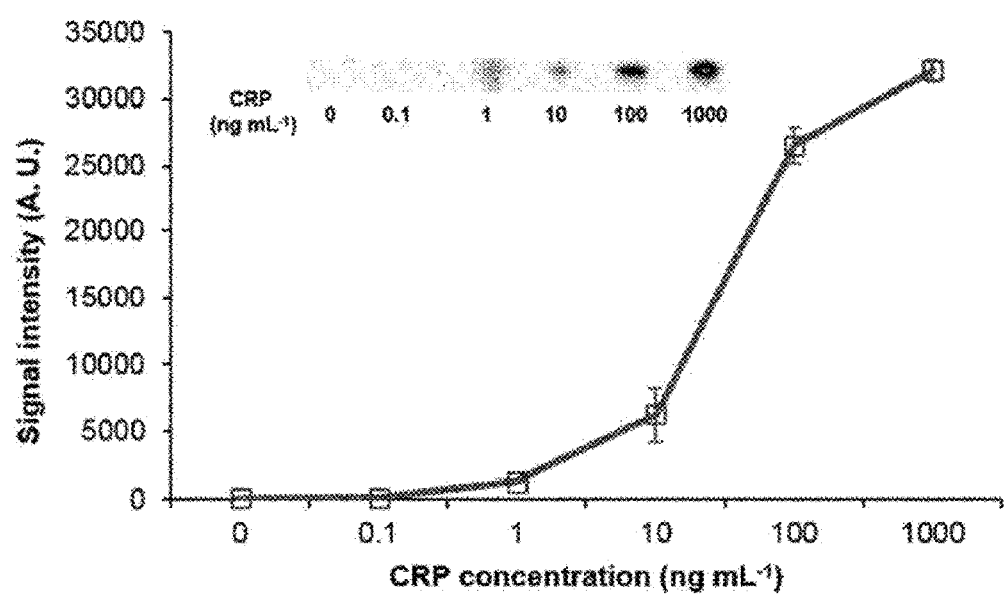
FIG. 13 is a graph showing results of measurement of CRP present in human serum using a membrane strip sensor according to an embodiment of the present disclosure.
Figure 14:
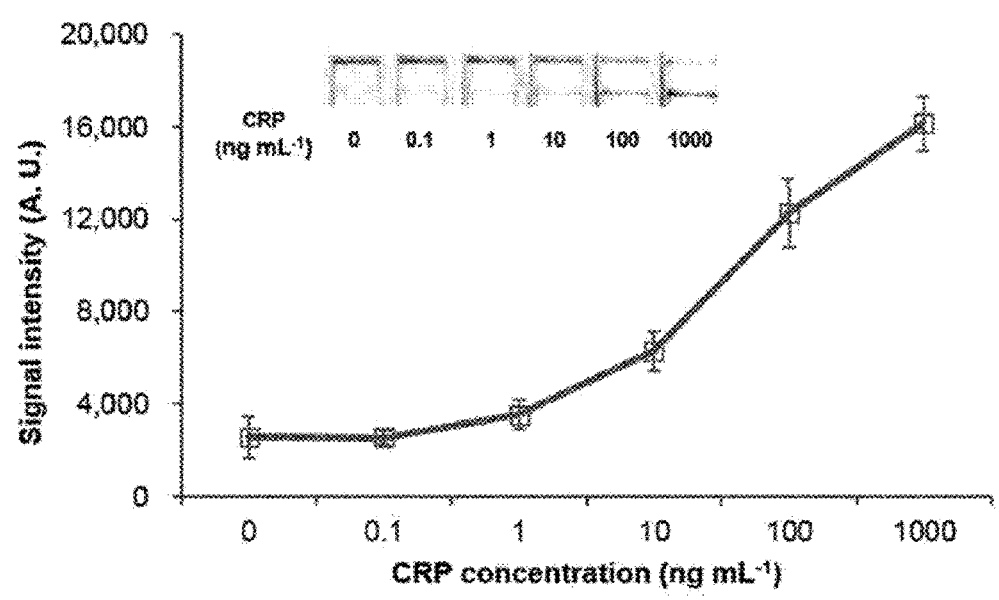
FIG. 14 is a graph showing results of measurement of CRP present in human serum using a conventional membrane strip sensor.

In order to detect the CRP, the serums injected with the CRPs with varying concentrations were used. After injecting the serum into the strip according to the present disclosure, the signal intensity of the chemiluminescence was measured for 20 minutes. FIG. 13 is a graph showing the CRP detection results for the membrane strip sensor according to the present disclosure. FIG. 14 is a graph showing the CRP detection results for the conventional membrane strip sensor. A limit of detection (LOD) (blank signal+3 standard deviations) was calculated to be 0.03 ng mL$^{-1}$, which is superior to a limit of detection for the conventional ICA which is 13.65 ng mL$^{-1}$.

Although embodiments of the present disclosure have been described with reference to the accompanying drawings, those skilled in the art will appreciate that the present disclosure may be embodied in other specific forms without departing from the spirit or essential characteristics thereof.

Therefore, it should be considered that the embodiments disclosed herein are illustrative in all aspects and not restrictive. The scope of the present disclosure is to be interpreted by the appended claims rather than the foregoing description, and all changes or modifications derived from the meaning and scope of the claims and equivalents thereof to be within the scope of present disclosure.

| REFERENCE NUMERALS | |
|---|---|
| 110: support | 120: sample pad |
| 130: conjugate pad | 140: reaction membrane |
| 150: absorption pad | 161: secondary reagent pad |
| 162: swelling portion | 163: connecting membrane |
| 164: support pad | 165: intermediate membrane |

What is claimed is:

1. A membrane strip sensor comprising:
a support;
a sample pad attached to a top face of the support to receive a liquid sample to be analyzed;
an intermediate membrane serving to transfer the liquid sample received from the sample pad to a swellable portion;
a conjugate pad interlocking with the sample pad, and containing a primary reagent, wherein the primary reagent specifically binds to an analyte contained in the liquid sample through the sample pad;
a reaction membrane detecting whether or not the analyte is present in the liquid sample and interlock with the conjugated pad;
a absorption pad which is disposed downstream of the reaction membrane and absorbs the liquid sample for which a detection reaction is terminated; and
a secondary reagent pad which connected to the swellable portion and is in contact with the reaction membrane by swelling of the swellable portion, wherein the secondary reagent pad is spaced apart from the reaction membrane, and the swellable portion swells by the liquid sample contained in the sample pad,
wherein
the sample pad, the intermediate membrane, the conjugate pad, the reaction membrane, and the absorption pad are laterally sequentially placed on the support,
the sample pad forwards the liquid sample to the intermediate membrane or the reaction membrane,
the intermediate membrane is in direct contact with the sample pad and not in direct contact with the secondary reagent pad,
the secondary reagent pad does not directly contact with the sample pad, and the secondary reagent pad is connected to the sample pad via the intermediate membrane, and
the intermediate membrane is a porous membrane, and the liquid sample moves through the pores.

2. The membrane strip sensor according to claim 1, wherein the swellable portion is joined to be supported by a support pad attached on the intermediate membrane disposed between the conjugate pad and the sample pad, and the swellable portion is attached to a connecting membrane is spaced apart from the reaction membrane by a predetermined distance.

3. The membrane strip sensor according to claim 1, wherein the swellable portion is made of a plastic material having pores defined therein to allow the swellable portion to be swollen by liquid which is adsorbed thereto.

4. The membrane strip sensor according to claim 3, wherein the swellable portion is made of a water-soluble plastic material.

5. The membrane strip sensor according to claim 4, wherein the water-soluble plastic material includes at least one selected from a group consisting of polyvinyl alcohol (PVA), polyacrylamide (PAM), methylolated urea resin, methylolated melamine resin, and carboxymethyl cellulose (CMC).

6. The membrane strip sensor according to claim 1, wherein the intermediate membrane has a structure in which a large pore portion and a small pore portion are in a asymmetric structure, and the small pore portion is positioned toward the support pad.

7. The membrane strip sensor according to claim 2, wherein the connecting membrane has a structure in which a large pore portion and a small pore portion are in a asymmetric structure, and the small pore portion is positioned toward the swellable portion.

8. The membrane strip sensor according to claim 1, wherein a primary reagent reacting with the sample is applied to the conjugate pad, and a secondary reagent generating a signal is applied to the secondary reagent pad.

9. The membrane strip sensor according to claim 8, wherein the primary reagent is one or a conjugate of two or more selected from a group consisting of antibody, antigen, enzyme, peptide, protein, DNA, RNA, PNA, aptamer and nanoparticle.

10. The membrane strip sensor according to claim 8, wherein the secondary reagent is at least one selected from a group consisting of a light absorbing substance, a fluorescence substance, a luminous substance, an electrochemical signal generating substance, and a signal amplifying substance amplifying an intensity of an absorbance, fluorescence, luminescence or electrochemical signal.

* * * * *